US009434772B2

(12) United States Patent
Maurelli (10) Patent No.: US 9,434,772 B2
(45) Date of Patent: Sep. 6, 2016

(54) *SHIGELLA*-DERIVED VECTOR AND METHODS OF USING THE SAME (75) Inventor: Anthony T. Maurelli, Silver Spring, MD (US)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 0 days.

(21) Appl. No.: 14/346,408

(22) PCT Filed: Sep. 13, 2012

(86) PCT No.: PCT/US2012/055097
§ 371 (c)(1),
(2), (4) Date: Mar. 21, 2014

(87) PCT Pub. No.: WO2013/043459
PCT Pub. Date: Mar. 28, 2013

(65) Prior Publication Data
US 2014/0220072 A1 Aug. 7, 2014

Related U.S. Application Data (60) Provisional application No. 61/537,612, filed on Sep. 22, 2011.

(51) Int. Cl.
| | |
|---|---|
| A61K 39/02 | (2006.01) |
| C12N 1/20 | (2006.01) |
| C12N 15/00 | (2006.01) |
| A61K 39/00 | (2006.01) |
| A61K 39/38 | (2006.01) |
| C07K 14/25 | (2006.01) |
| A61K 39/112 | (2006.01) |
| C12N 15/70 | (2006.01) |
| C12N 15/74 | (2006.01) |
| A61K 38/00 | (2006.01) |
| C12N 15/86 | (2006.01) |

(52) U.S. Cl.
CPC ........... *C07K 14/25* (2013.01); *A61K 39/0283* (2013.01); *C12N 15/70* (2013.01); *C12N 15/74* (2013.01); *A61K 38/00* (2013.01); *A61K 39/00* (2013.01); *A61K 2039/522* (2013.01); *C12N 15/86* (2013.01)

(58) Field of Classification Search
CPC ........... A61K 2039/522; A61K 38/00; C12N 15/86; C12N 15/70
See application file for complete search history.

(56) References Cited

U.S. PATENT DOCUMENTS

2008/0267998 A1 10/2008 Venkatesan et al.
2011/0165680 A1 7/2011 Blattner et al.

OTHER PUBLICATIONS

Kato et al., Infection and Immunity, 1989; 57(5): 1391-98.*
Le Gall et al., Microbiology, 2005; 151: 951-962.*
Stills, ILAR Journal, 2005; 46(3): 280-293.*
Adler, B. et al. A dual transcriptional activation system for the 230 kb plasmid genes coding for virulence-associated antigens of Shigella flexneri. Molecular Microbiology, 1959, vol. 3, No. 5, pp. 627-635.
Peng, Junping et al. The molecular evolutionary history of *Shigella* spp. and enteroinvasive *Escherichia coli*. Infection, Genetics and Evolution, 2009, vol. 9, pp. 147-452.
Buchrieser, Carmen et al. The virulence plasmic pWR100 and the repertoire of proteins secreted by the type III secretion apparatus of Shigella flexneri. Molecular Microbiology, 2000, vol. 38, No. 4, pp. 760-771.
Sansonetti, P.J. et al. Involvement of a Plasmid in the Invasive Ability of Shigella flexneri. Infection and Immunity, Mar. 1982, pp. 852-860.
Sakai, T. et al. Expression of four virulence antigens of Shigella flexneri is positively regulated at the transcriptional level by the 30 kiloDalton virF protein, Molecular Microbiology, 1988, vol. 2, No. 5, pp. 589-597.
Yang, Fan et al. Genome dynamics and diversity of *Shigella* species, the etiologic agents of bacillary dysentery. Nucleic Acids Research, 2005, vol. 33, No. 9, pp. 6445-6458.
Jennison, Amy V. et al. Shigella flexneri infection: pathogenesis and vaccine development. FEMS Microbiology Review, 2994, vol. 28, pp. 43-58.
Amidi, Maryam et al. Antigen-expressing immunostimulatory liposomes as a genetically programmable synthetic vaccine, Syst. Synth. Biol., 2011, vol. 5, pp. 21-31.
Paetzold, Susanne et al. Shigella fexneri Phagosornal Escape Is Independent of Invasion. Infection and Immunity, Oct. 2007, vol. 75, No. 10, pp. 4826-4830.
Venkatesan, Malabi M. et al. Complete DNA Sequence and Analysis of the Large Virulence Plasmic of Shigella flexneri, Infection and Immunity, May 2001, vol. 69, No. 5, pp. 3271-3285.
Maurelli, Anthony T. et al. Temperature-Dependent Expression of Virulence Genes in *Shigella* Species. Infection and Immunity, Jan. 1874, vol. 43, No. 1, pp. 195-201.
Kotloff, Karen L. et al, Shigella flexneri 2a Strain CVD 1207, with Specific Deletions in virG, sen, set, and guaBA, is Highly Attenuated in Humans. Infections and Immunity, Mar. 2000, vol. 68, No. 3, pp. 1034-1039.
Coster, Trinka S. et al. Vaccination against Shigellosis with Attenuated Shigella flexneri 2a Strain SC602. Infection and Immunity, Jul. 1999, vol. 67, No, 7, pp. 3437-3443.

(Continued)

Primary Examiner — Gary Nickol
Assistant Examiner — Lakia Tongue
(74) Attorney, Agent, or Firm — MH2 Technology Law Group, LLP (57) ABSTRACT Recombinant vectors comprising the cell entry region of the *Shigella* ox EIEC invasion plasmid are provided, as well as, *Shigella* or EIEC strains comprising the recombinant vectors. The vectors provide an improved platform for developing attenuated vaccine strains of *Shigella* or EiEC and for delivering other foreign proteins of interest. The recombinant vectors and bacterial strains comprising the same may be used in methods of inducing an immune response.

17 Claims, 8 Drawing Sheets (56) References Cited

OTHER PUBLICATIONS

Levine, Myron M. et al. Clinical trials of Shigella vaccines: two steps forward and one step back on a long, hard road. Nature Reviews, Microbilogy, Jul. 2007, vol. 5, pp. 540-553.

Supplementary European Search Report dated Mar. 27, 2015 from European Application No. 12833989.2, pp. 1-10.

Menard, Robert et al. Nonpolar Mutagenesis of the ipa Genes Defines IpaB, IpaC, and IpaD as Effectors of Shigella flexner Entry into Epithelial Cells. Journal of Bacteriology. Sep. 1993, vol. 175, No. 18, pp. 5899-5906.

Santapaola, Daniela et al. Enteroinvasive *Escherichia coli* virulence-plasmid-carried apyrase (apy) and ospB genes are organized as a bicistronic operon and are subject to differential expression. Microbiology, Aug. 1, 2002, vol. 148, No. 8, pp. 2519-2529.

Noriega, Fernando R. et al. Strategy for Cross-Protection among Shigella flexneri Serotypes. Infection and Immunity, Feb. 1999, vol. 67, No. 2, pp. 782-788.

Venkatesan, M. et al. Virulence phenotype and genetic characteristics of the T32-ISTRATI Shigella flexnari 2a vaccine strain. Vaccine, May 1991, vol. 9, pp. 358-363.

Sasakawa, Chihiro et al. Virulence-Associated Genetic Regions Comprising 31 Kilobases of the 230-Kilobase Plasmid in Shigella flexneri 2a. Journal of Bacteriology, Jun. 1988, vol. 170, No. 6, pp. 2480-2484.

Torres, Alfredo G. Currents aspects of Shigella pathogenesis. Microbiologia, Jul. 2004, vol. 46, Nos. 3-4, pp. 89-97.

Phalipon, Armelle et al. Shigellosis Innate Mechanisms of Inflammatory Destruction of the Intestinal Epithellum, Adaptive Immune Response, and Vaccine Development. Critical Reviews in Immunology, Jan. 2003, vol. 23. No. 5/6, pp. 371-401.

\* cited by examiner

SHIGELLA-DERIVED VECTOR AND METHODS OF USING THE SAME

CROSS-REFERENCE TO RELATED APPLICATIONS

This application is a U.S. National Stage application of PCT/US2012/055097 filed 13 Sep. 2012, which claims the benefit of, and relies on the filing date of, U.S. provisional patent application No. 61/537,612, filed 22 Sep. 2011, the entire disclosure of which is incorporated herein by reference.

GOVERNMENT INTEREST

This invention was made in part with Government support under grant R01 AI24656-18 awarded by the National institute of Allergy and Infectious Diseases. The U.S. Government has certain rights in this invention.

BACKGROUND

Live, attenuated strains of bacteria have been successfully used as vaccines to protect humans and animals from disease. The successful vaccine strain is modified to reduce its ability to cause disease to an acceptable level while it retains sufficient pathogenic potential to stimulate a protective immune response in the vaccinated host. Therefore a delicate balance must be achieved as extensive attenuation generally results in reduced immunity.

*Shigella* is a genus of Gram-negative bacteria belonging to the family Enterobacteriaceae and the etiologic agent of bacillary dysentery or shigellosis, the symptoms of which include abdominal pain, diarrhea, fever, vomiting, and blood or mucus in the stool. *Shigella* is transmitted by a fecal-oral route, typically through contaminated food or water. As a result, *Shigella* is more of a public health threat in developing countries where proper sanitation and hygiene are lacking.

The development of an effective live, attenuated strain of *Shigella* to protect humans against bacillary dysentery (shigellosis) has been hampered by the inability to strike a balance between a need for the strain to invade the intestinal epithelium and reduction of pathogenicity to an acceptable level. Invasive strains that are protective tend to be "reactogenic," i.e., they cause diarrhea and/or fever in the host.

The current strategy used by most investigators to attenuate *Shigella* is to mutate or delete genes on the *Shigella* invasion plasmid in the hopes of reducing the reactogenicity of the vaccine strain while preserving immunogenicity. Levine, M. et al. 2007. Clinical trials of *Shigella* vaccines: two steps forward and one step back on a long, hard road. Nat Rev Microbial 5:540-553. This strategy is a "top-down" approach starting with a wild type, virulent strain of *Shigella*. Genes are then systematically inactivated until the strain is sufficiently attenuated to be clinically safe to administer yet still stimulate a robust immune response. For example, the attenuating mutation in *S. flexneri* 2a strain SC602 is a deletion of virG(icsA) which abolishes the ability of the bacterium to spread from cell to cell after invasion. Coster, T. S. et al. 1999. Vaccination against shigellosis with attenuated *Shigella flexneri* 2a strain SC602. Infect. Immun. 67:3437-3443. A gene on the invasion plasmid that encodes an enterotoxin and another enterotoxin gene on the chromosome were targets in construction of *S. flexneri* 2a strain CVD1207 leading to attenuation and reduced reactogenicity. Kotloff, K. L. et al. 2000. *Shigella flexneri* 2a strain CVD 1207, with specific deletions in virG(icsA), sen, set, and guaBA, is highly attenuated in humans. Infect Immun 68:1034-1039.

A major disadvantage of this "top down" strategy is that the attenuated strains that are protective have the undesirable side effect of causing diarrhea and/or fever. Further, to achieve the appropriate balance in the "top down" approach between preserving immunogenicity and reducing reactogenicity, other genes on the invasion plasmid (also known as the virulence plasmid), and possibly the chromosome as well, that may contribute to reactogenicity must be identified and inactivated.

SUMMARY

In contrast to the prior "top down" strategy, the vectors described in this application were designed using a much more challenging "bottom up" strategy, starting with the minimal set of genes from the *Shigella* invasion plasmid that mediate invasion of and multiplication within host epithelial cells. These genes were cloned into a plasmid to produce *Shigella* minimal invasion plasmid (SMIP). The SMIP can be transferred into a plasmid-cured strain of *Shigella* or an enteroinvasive *Escherichia coli* (EIEC), where it can be used as a vaccine strain. Additionally, the SMIP can serve as a platform to which other genes can be added in an attempt to improve immunogenicity of the vaccine strain. This strategy is an improvement over the "top-dawn" strategy because it allows one to directly determine the contribution of any putative virulence gene by adding it back to the SMIP, i.e., the role of the gene can be measured in the context of the minimal gene complement required for invasion rather than in the larger context of all of the genes normally present on the invasion plasmid.

The vectors and bacterial strains described in this application provide an improved platform for developing a live, attenuated vaccine strain of *Shigella* or EIEC that achieves the balance between immunogenicity and reduced reactogenicity in volunteers. In addition to inserting other *Shigella* or EIEC genes into the SMIP, it is also possible to insert a gene that encodes an immunogenic protein from a pathogen other than *Shigella* or EIEC or some other non-*Shigella* or non-EIEC protein of interest. In other words, a plasmid-cured *Shigella* or EEC strain comprising the SMIP can be used as a broad antigen delivery system for delivering any antigen of interest. *Shigella* or EIEC invasion into colonic mucosa stimulates a strong immune response in the intestinal mucosa. Furthermore, *Shigella* or EIEC invasion in the colon can also stimulate lymphoid tissues adjacent to the colon, and, thus, it could stimulate a strong mucosal immune response in the reproductive tract. Thus, the SMIP can be used as a live vaccine platform for delivery or expression of recombinant antigens in host cells. That is, the SMIP can be used as a vehicle for delivering DNA vaccines to mucosal lymphoid tissues or for expression and delivery of recombinant antigens.

As such, the SMIP can be used in methods of inducing an immune response in a subject. In one embodiment, the immune response is directed to *Shigella*. In other embodiments, the immune response is directed to a bacterial, viral, fungal, parasitic, or mammalian protein of interest.

BRIEF DESCRIPTION OF THE DRAWINGS

The accompanying drawings, which are included to provide a further understanding of the invention and are incorporated in and constitute a part of this specification, illustrate aspects of the invention and together with the description serve to explain the principles of the invention. In the drawings:

FIG. 1 shows the geometric mean titers (GMT) of mucosal IgA responses in naïve guinea pigs or guinea pigs immunized with SMIP or SMIP+virG(icsA) ("SMIP/G"). Upper and lower error bars together represent one standard deviation from the GMT. A. Mucosal IgA response to Invaplex (crude water-extracted *Shigella*). B. Mucosal IgA response to LPS.

FIG. 2 shows the geometric mean titers (GMT) of serum IgA responses in naïve guinea pigs or guinea pigs immunized with SMIP or SMIP+virG(icsA) ("SMIP/G"). Upper and lower error bars together represent one standard deviation from the GMT. A. Serum IgA response to Invaplex. B. Serum IgA response to LPS.

FIG. 3 shows the geometric mean titers (GMT) of serum IgG responses in naïve guinea pigs or guinea pigs immunized with SMIP or SMIP+virG(icsA) ("SMIP/G"). Upper and lower error bars together represent one standard deviation from the GMT. A. Serum IgG response to Invaplex. B. Serum IgG response to LPS.

DETAILED DESCRIPTION

Reference will now be made in detail to various exemplary embodiments. It is to be understood that the following detailed description is provided to give the reader a fuller understanding of certain embodiments, features, and details of aspects of the invention, and should not be interpreted as a limitation of the scope of the invention.

1. Definitions

In order that the present invention may be more readily understood, certain terms are first defined. Additional definitions are set forth throughout the detailed description.

As used in this application, the term "foreign protein" refers to a protein, or an immunogenic portion thereof, that is from a source other than *Shigella* or EIEC.

As used in this application, the term "cell entry region" refers to an approximately 30 kilobase pair region of the invasion plasmid of a *Shigella* bacterium or an EIEC that includes an ipa gene locus, an ipg gene locus, a virB gene, and a mxi-spa gene locus.

As used in this application, the abbreviation "EIEC" refers to enteroinvasive *Escherichia coli*.

As used in this application, the term "origin of replication" refers to a nucleic acid from which nucleic acid replication is initiated. The origin of replication helps to control the number of copies of the vector in the host cell. Such sequences are well known for a variety of plasmids, bacteria, yeast and viruses. A low copy origin of replication yields from 1 to about 10 copies of the vector per cell. A high copy origin of replication yields from about 20 to about 200 copies of the vector per cell.

As used in this application, the term "plasmid-cured" refers to a bacterial strain (e.g., *Shigella* or EIEC) from which the invasion plasmid has been removed or otherwise inactivated. The invasion plasmid can be removed from the bacterial strain using known methods, including, for example, using a curing agent, such as acridine orange, to eliminate the invasion plasmid from the bacterial strain.

As used in this application, the term "recombinant vector" refers to a vector constructed, using laboratory methods, of nucleic acids from multiple sources and specifically excludes a wild type *Shigella* or EIEC invasion plasmid or a wild type *Shigella* or EIEC invasion plasmid that has been mutated to delete or inactivate one or more genes on the invasion plasmid.

As used in this application, the term "selection gene," refers to a gene, such as an antibiotic resistance gene, used in a recombinant vector that encodes a protein whose expression permits the selection of host cells containing the recombinant vector. The wild type invasion plasmid does not contain a selection gene, as the term is used in this application.

As used in this application, the term "vector" refers to an autonomously replicating nucleic acid unit and includes plasmid vectors, viral vectors, bacteriophage vectors, cosmid vectors, fosmid vectors, and phasmid vectors.

As used in this application, the term "invasion plasmid" refers to a plasmid of about 220 kilobases found in virulent strains of *Shigella* and EIEC that encodes numerous genes that mediate different aspects of *Shigella* or EIEC host cell invasion and virulence. The invasion plasmid is also referred to interchangeably in the art as the virulence plasmid.

2. *Shigella*

*Shigella* is a genus of Gram-negative bacteria belonging to the family Enterobacteriaceae and the etiologic agent of bacillary dysentery or shigellosis, the symptoms of which include abdominal pain, diarrhea, fever, vomiting, and blood or mucus in the stool. There are four species of *Shigella*: *Shigella dysenteriae*, *Shigella flexneri*, *Shigella boydii*, and *Shigella sonnei* (also referred to as serogroups A, B, C, and D, respectively). *Shigella* is transmitted by a fecal-oral route, typically through contaminated food or water.

*Shigella* is very closely related to enteroinvasive *Escherichia coli* (EIEC), which also cause dysentery, with recent evidence suggesting that *Shigella* and EIEC are derived from multiple origins of *E. coli* and form a single pathovar. Yang et al., (2005) Nucleic Acids Res., 33(19):6445-58. Certain O-antigens associated with EIEC are identical to those found in *Shigella* spp. and many plasmid-associated virulence determinants are common to both EIEC and *Shigella*. Id. *Shigella* and EIEC invade colonic epithelial multiply intracellularly, and spread to neighboring cells. The genetic elements responsible for these invasive properties are located on the bacterial chromosome and on a large (about 220 kb) plasmid called the invasion or virulence plasmid that is unique to the virulent strains of *Shigella* and EIEC. *Shigella* variants that have lost the invasion plasmid also lose their invasive properties. The invasion plasmid encodes several known or putative virulence genes including:

| Product | Gene | Function |
|---|---|---|
| Type III secretion system (T3SS) | mxi-spa region | Secretion and injection of effectors into host cell; mediates invasion and host cell signaling |
| T3SS secreted proteins | ipaA | Vinculin activation; actin depolymerization; modulates formation of microspikes |
| | ipaB | Translocon pore and tip complex protein; invasion; vacuole escape; apoptosis induction; controls flux of proteins through T3S needle |
| | ipaC | Translocon pore protein (with IpaB); invasion; actin polymerization, activation of Cdc42 and Rac |
| | ipaD | Tip complex protein (with IpaB); invasion; controls flux of proteins through T3S needle |
| | ipgD | Phosphotidylinositol 4-phosphatase; membrane blebbing |
| | icsB | Camouflaging VirG(IcsA) from autophagic host defense system |
| | virA | Cysteine protease; microtubule destabilization and membrane ruffling |
| | ospF | Phosphothreonine lyase; inhibits histone phosphorylation and NF-κB-dependent gene expression |
| | ipaH7.8 | Facilitates escape of bacteria from phagocytic vacuole of macrophage |
| | ipaH4.5 | Unknown |
| | ipgB1 and ipgB2 | Induce membrane ruffling by activation of Rac1 and Cdc42 |
| | ospG | Protein kinase; interferes with activation of the NF-κB pathway |
| | ospB | Induction of PMN migration |
| | ospC1 | Induction of PMN migration |
| | ospZ | Induction of PMN migration |
| Toxins | | |
| ShET2 | senA | Ion secretion |
| | senB | Homologues of ShET2 |
| Enzymes | icsP/sopA | Serine protease; cleavage of VirG(IcsA) |
| | sepA | Serine protease; tissue invasion |
| | msbB | Fatty acyl modification of O antigen |
| | apy | ATP-diphosphohydrolase |
| | phoN-Sf | Non-specific acid phosphatase |
| | rfbU | O-antigen biosynthesis |
| | ushA | UDP-sugar hydrolase (5' nucleotidase) |
| Regulators | virF | Transcriptional regulation of virB and virG(icsA) expression |
| | virK | Post-transcriptional regulation of virG(icsA) expression |
| | virB | Transcriptional activation of ipa, spa, and mxi operons |
| Other | virG(icsA) | Nucleation of actin filaments; intracellular and intercelltilar motility |

From Yang et al., (2005) Nucleic Acids Res., 33(19)6445-58. In addition to the invasion plasmid, many chromosomal genes also contribute to virulence, including set1A, set1B (enterotoxin), iucA-D (aerobactin production and transport), iutA (iron uptake), pic (serine protease/mucinase), and sigA (protease).

Virulence of *Shigella* is dependent on temperature. At 37° C. *Shigella* are fully virulent, whereas at 30° C. *Shigella* lose the ability to both invade epithelial cells and provoke keratoconjunctivitis in guinea pigs. Maurelli et al., (1984) Infect. Immun. 43(1):195-201. When *Shigella* grows at 37° C., the VirF protein induces the expression of the VirB protein, which in turn activates the ipa, mxi, and spa promoters, causing the activation of the spa and mxi operons. This results in the synthesis of a protein complex called the Mxi-Spa translocon. Contact between the bacterium and the host epithelial cell activates the translocon, leading to the secretion of invasion plasmid antigens (Ipa). IpaA, IpaB, and IpaC form a complex that interacts with the cellular membrane and induces a signal cascade that causes the bacterium to be internalized into the cytoplasm via an endosome. The Ipa proteins also mediate the release of the bacterium from the endosome.

Figure 5:
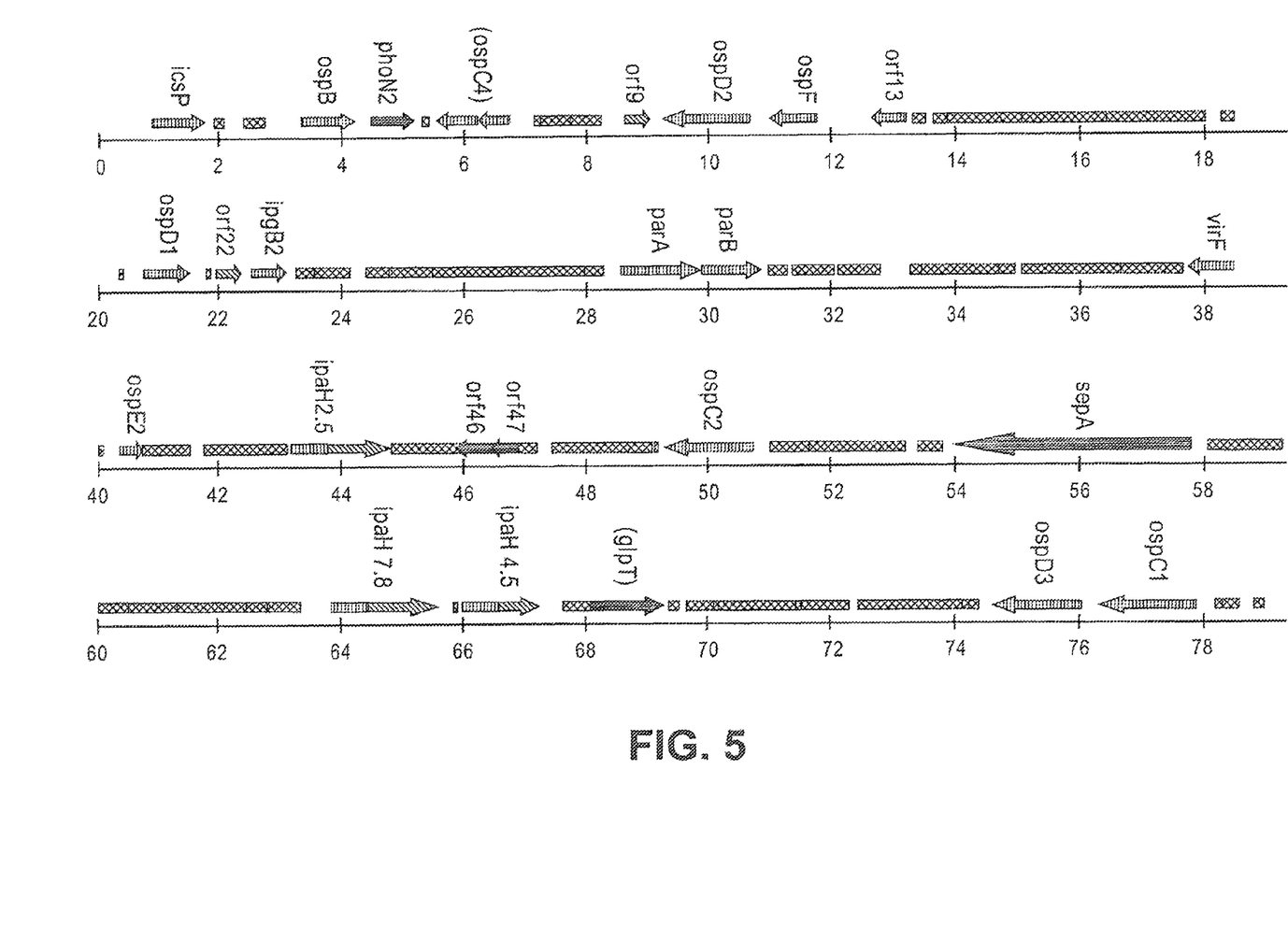
FIG. 5 shows the genes located on the approximately 220 kilobase pair invasion plasmid of *Shigella flexneri*.
Figure 6:
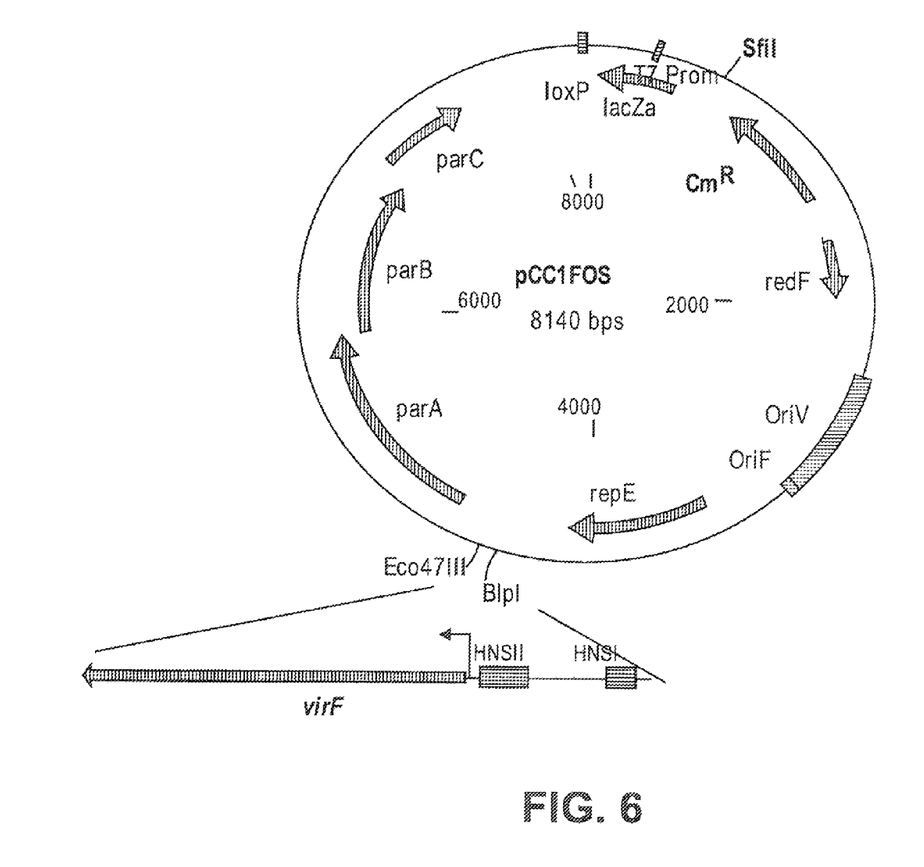
FIG. 6 shows a plasmid map of a SMIP vector where the cell entry region was inserted into a SfiI restriction site on the pCC1FOS plasmid. The plasmid contains an *E. coli*, single copy origin of replication, F1 incompatibility group (OriF) and a high copy origin of replication (OriV) that allows replication about 20-200 copies when induced in *E. coli* EPI300.

A cell entry region of about 30 kb is generally conserved in invasion plasmids and includes the mxi-spa gene locus, the virB gene, the ipa gene locus, and the ipg gene locus. Yang et al., (2005) Nucleic Acids Res., 33(19)6445-58. See FIG. 5. The cell entry region is bracketed by insertion sequence 100 and insertion sequence 600 in all invasion plasmids, suggesting the transmission of a common invasion plasmid in *Shigella* or the transmission of a cell entry region to all invasion plasmids from a common source. Yang et al., (2005) Nucleic Acids Res., 33(19):6445-58. The cell entry region has the markings of a typical pathogenicity island (PAI), such as G+C content distinctly different from the surrounding genes, indicating genetic instability. The remaining ~190 kb of virulence plasmid DNA sequence has a mosaic character. It contains genes related to IncFIIA-type plasmids. In addition, the plasmid is littered with copies of IS elements and remnants of IS elements that account for 53% of the open reading frames on the plasmid as well as a class of virulence genes known as the osp genes. These virulence genes encode secreted effector molecules that are transported by the type III secretion system (T3SS). Given the unusual mosaic makeup of the virulence plasmid, it is likely that it was formed by sequential gene acquisition and possibly gene duplication and rearrangement. The presence of three separate and distinct ospD genes on the *S. flexneri* 2a plasmid is evidence that argues for gene duplication after gene acquisition. In any event, it is apparent that the virulence plasmid present in contemporary strains of *Shigella* spp. arose in a step-wise fashion.

In addition to invasion, a fully virulent strain of *Shigella* has several other hallmark phenotypes, including intracellular replication, intercellular spread, the ability to induce apoptosis in macrophages, the ability to protect a host mammalian cell from apoptosis, the ability to signal polymorphonuclear leukocyte migration across a model monolayer of polarized epithelial cells, and the ability to generate a strong inflammatory reaction in the guinea pig model for keratoconjunctivitis (Serény test). Post-invasion phenotypes are important for full virulence and the state of the art for identifying genes responsible for these phenotypes has been to inactivate a gene and test for loss or reduction of virulence phenotypes.

3. Vectors

The present disclosure provides a recombinant vector comprising the cell entry region of a *Shigella* or EIEC invasion plasmid and a virF gene from a *Shigella* or EIEC invasion plasmid and optionally a selection gene. In one embodiment, the cell entry region is from a *Shigella flexneri* invasion plasmid. In another embodiment, the vector comprises a *Shigella* cell entry region located between insertion sequence 100 and insertion sequence 600 of a *Shigella* invasion plasmid. In yet another embodiment, the recombinant vector comprises an ipa gene locus from a *Shigella* or EIEC invasion plasmid, an ipg gene locus from a *Shigella* or EIEC invasion plasmid, a virB gene from a *Shigella* or EIEC invasion plasmid, a mxi-spa gene locus from a *Shigella* or EIEC invasion plasmid, and a virF gene from a *Shigella* or EIEC invasion plasmid.

The recombinant vector is capable of directing the expression of genes that have been inserted into the vector. Thus, in certain aspects, the recombinant vector further comprises a nucleic acid encoding one or more foreign proteins, including, for example, one or more bacterial viral, fungal, parasitic, or mammalian proteins, or an immunogenic portion thereof. The recombinant vector can be used to express any protein of interest. In one embodiment, the protein is from an enterohemorrhagic or enterotoxigenic *E. coli*, including, but not limited to the intimin protein, the colonization factor antigen I fimbrial adhesion, or the heat labile toxin (LT) subunit B. In another embodiment, the protein is from *Salmonella*, including, for example, a type III secretion system-1 secreted protein. In yet another embodiment, the protein is from *Vibrio cholerae*, including, for example, the cholera toxin subunit B. In another embodiment, the protein is from *Yersinia pestis*, including, for example, the F1 capsular protein or the LorV (V antigen).

In another aspect, the recombinant vector further comprises a nucleic acid encoding one or more *Shigella* or EIEC proteins, or an immunogenic portion thereof, including, but not limited to, a virG(icsA) gene, an osp gene (e.g., ospB, ospF, ospD, ospC, ospZ), a virA gene, a virK gene, an ipaH gene, a phoN gene, a senA or senB gene, an icsP/sopA gene, a sepA gene, an msbB gene, an apy gene, a rfbU gene, a ushA gene, a stxAB gene, a set1A or set1B gene, a pic gene, a sigA gene, an iutA or iucABCD gene, an iroN or iroBCDE gene, a sitABCD gene, a shuA, shuS, or shuTWXYUV gene, an ipaH, a yadA-like gene, a clp-like gene, an IcmF-like gene, an RTX-like gene, or a gspC-M gene. In another embodiment, the recombinant vector further comprises a second nucleic acid encoding a *Shigella* protein, or an immunogenic portion thereof, wherein the *Shigella* protein is not encoded by an ipa gene locus, an ipg gene locus, a virB gene, a mxi-spa gene locus, a virF gene, or a virG(icsA) gene. In a preferred embodiment, the recombinant vector further comprises a virG(icsA) gene. In other embodiments, the recombinant vector does not contain an osp gene from a *Shigella* or EIEC bacterium. Those embodiments in which the recombinant vector comprises a first nucleic acid encoding one or more *Shigella* or EIEC proteins, or an immunogenic portion thereof, may further comprise a second nucleic acid encoding a foreign protein.

The nucleic acid encoding the one or more bacterial, viral, fungal, parasitic, or mammalian proteins, or an immunogenic portion thereof or the one or more *Shigella* or EIEC proteins, or an immunogenic portion thereof, may be inserted into a replicable vector for cloning (amplification of the DNA) or for expression. Various vectors are publicly available. The appropriate nucleic acid sequence may be inserted into the vector by a variety of procedures known in the art. For example, DNA may be inserted into an appropriate restriction endonuclease site(s) in the vector using techniques known in the art.

As compared to other mutated *Shigella* invasion plasmids generated using a "top down" approach (Coster, T. S. et al., Infect. Immun. 67:3437-3443; Kotloff, K. L. et al. 2000. Infect Immun 68:1034-1039. Levine, M. M. et al., Nat Rev Microbiol 5:540-553), the recombinant vectors provided in this application contain a substantially smaller portion of the invasion plasmid. In one embodiment, the recombinant vector comprises no more than about 30, 40, 50, 60, 70, 80, 90, 100, 110, 120, 130, 140, 150, 160, 170, 180, 190, or 200 kilobase pairs of a *Shigella* or EIEC invasion plasmid. Preferably the recombinant vector comprises no more than about 30-50 kilobase pairs of the invasion plasmid. The recombinant vectors disclosed herein can also be much smaller in overall size than the mutated invasion plasmids generated using the "top down" approach. Thus, in certain embodiments, the recombinant vector has no more than about 40, 50, 60, 70, 80, 90, 100, 110, 120, 130, 140, 150, 160, 170, 180, 190, or 200 kilobase pairs. Preferably the recombinant vector has no more than about 40-100 kilobase pairs. More preferably the recombinant vector has no more than about 40-60 kilobase pairs.

Suitable vectors may be chosen or constructed to contain appropriate regulatory sequences, including promoter sequences, terminator sequences, enhancer sequences, a selection gene, and other sequences. Typical selection genes encode proteins that (a) confer resistance to antibiotics or other toxins, e.g., ampicillin, neomycin, kanamycin, chloramphenicol, or tetracycline, (b) complement auxotrophic deficiencies, or (c) supply critical nutrients not available from complex media, e.g., the gene encoding D-alanine racemase. Such selection genes are well known in the art. Construction of suitable vectors containing one or more of these regulatory sequences employs standard ligation techniques which are known to the skilled artisan. See e.g., Sambrook et al., Molecular Cloning: A Laboratory Manual, 3rd ed., Cold Spring Harbor Laboratory Press (2001). Many established techniques used with vectors, including the manipulation, preparation, mutagenesis, sequencing, and transfection of DNA, are described in Current Protocols in Molecular Biology, Ausubel et al. eds., John Wiley & Sons (2010).

In certain embodiments, the recombinant vector includes one or more origins of replication. In one embodiment, the vector comprises a low copy origin of replication (from 1-10 copies/cell), including, but not limited to the origin from plasmid pSC101, the origin of replication from the *Shigella* invasion plasmid, or the *E. coli* F-factor origin of replication (OriF). In certain embodiments, the low copy origin of replication is a single copy origin of replication, such as the OriF. In another embodiment, the vector comprises a medium copy origin of replication (10-20 copies/cell), including, but not limited to p15A and Co1E1. In another embodiment, the vector comprises a high copy origin of replication (20-200 copies/cell), including, but not limited to pLU19 and OriV. In another embodiment, the vector comprises a low or medium copy origin of replication and a high copy origin of replication. The low, medium, or high copy origin of replication is optionally inducible.

4. Host Cells and Expression Systems

The disclosure further provides a host cell that comprises at least one recombinant vector described herein. Systems for cloning and expressing polypeptides in a variety of host cells are known in the art. In brief, suitable host cells include mammalian cells, insect cells, plant cells, yeast cells, or prokaryotic cells, e.g., *E. coli*. Preferably the host cell is a bacterium. More preferably, the host cell is a *Shigella* (e.g., *Shigella dysenteriae, Shigella flexneri, Shigella boydii*, and *Shigella sonnei*) or EIEC bacterium comprising the recombinant vector described in this application. In one embodiment, the *Shigella* or EIEC bacterium is a plasmid-cured bacterium that does not contain an invasion plasmid.

A further aspect of the disclosure provides a method of introducing the recombinant vector into a host cell. For eukaryotic cells, suitable transfection techniques may include calcium phosphate, DEAE-Dextran, electroporation, or liposome-mediated transfection. For bacterial cells, suitable techniques may include, but are not limited to, calcium chloride transformation, electroporation, and transfection using bacteriophage. These techniques are well known in the art. See e.g., Current Protocols in Molecular Biology, Ausubel et al. eds., John Wiley & Sons (2010). DNA introduction may be followed by a selection method (e.g., antibiotic resistance) to select cells that contain the vector.

5. Vaccine

The vectors and bacterial strains described in this application provide an improved platform for developing an attenuated vaccine strain of *Shigella* or EIEC that achieves the balance between immunogenicity and reduced reactogenicity in a subject.

In one embodiment, the attenuated strain is a plasmid-cured *Shigella* or EIEC comprising a recombinant vector as described in this application (hereinafter referred to as "vaccine strain"). As noted above, in one embodiment, the recombinant vector of the vaccine strain further comprises a nucleic acid encoding one or more foreign proteins, including, for example, one or more bacterial, viral, fungal, parasitic, or mammalian proteins, or an immunogenic portion thereof. As noted above, in another embodiment, the recombinant vector of the vaccine strain further comprises a nucleic acid encoding one or more *Shigella* or EIEC proteins, or an immunogenic portion thereof. Also disclosed is a composition comprising the vaccine strain, at least one pharmaceutically acceptable excipient, and optionally an adjuvant (hereinafter referred to as "vaccine composition").

The pharmaceutically acceptable excipient can be chosen from, for example, diluents such as starch, microcrystalline cellulose, dicalcium phosphate, lactose, sorbitol, mannitol, sucrose, methyl dextrins; binders such as povidone, hydroxypropyl methylcellulose, dihydroxy propylcellulose, and sodium carboxymethylcellulose; and disintegrants such as crospovidone, sodium starch glycolate, croscarmellose sodium, and mixtures of any of the foregoing. The pharmaceutically acceptable excipient can further be chosen from lubricants such as magnesium stearate, calcium stearate, stearic acid, glyceryl behenate, hydrogenated vegetable oil, glycerine fumerate and glidants such as colloidal silicon dioxide, and mixtures thereof. In some embodiments of the present invention, the pharmaceutically acceptable excipient is chosen from microcrystalline cellulose, starch, talc, povidone, crospovidone, magnesium stearate, colloidal silicon dioxide, sodium dodecyl sulfate, and mixtures of any of the foregoing. The excipients of the present invention can be intragranular, intergranular, or mixtures thereof.

The vaccine composition can be formulated as freeze-dried or liquid preparations according to any means suitable in the art. Non-limiting examples of liquid form preparations include solutions, suspensions, syrups, slurries, and emulsions. Suitable liquid carriers include any suitable organic or inorganic solvent, for example, water, alcohol, saline solution, buffered saline solution, physiological saline solution, dextrose solution, water propylene glycol solutions, and the like, preferably in sterile form. After formulation, the vaccine composition can be incorporated into a sterile container which is then sealed and stored at a low temperature (e.g., 4° C.), or it can be freeze dried.

The vaccine composition can be formulated in either neutral or salt forms. Pharmaceutically acceptable salts include the acid addition salts (formed with the free amino groups of the active polypeptides) and which are formed with inorganic acids such as, for example, hydrochloric or phosphoric acids, or organic acids such as acetic, oxalic, tartaric, mandelic, and the like. Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccine composition can comprise agents that enhance the protective efficacy of the vaccine, such as adjuvants. Adjuvants include any compound or compounds that act to increase an immune response to *Shigella* or to any antigen delivered by the recombinant vector, thereby reducing the quantity of antigen necessary in the vaccine, and/or the frequency of administration necessary to generate a protective immune response. Adjuvants can include for example, emulsifiers, muramyl dipeptides, pyridine, aqueous adjuvants such as aluminum hydroxide, chitosan-based adjuvants, and any of the various saponins, oils, and other substances known in the art, such as Amphigen, LPS, bacterial cell wall extracts, bacterial DNA, CpG sequences, synthetic oligonucleotides and combinations thereof (Schijns et al. (2000) Curr. Opin. Immunol. 12:456), Mycobacterialphlei (*M. phlei*) cell wall extract (MCWE) (U.S. Pat. No. 4,744,984), *M. phlei* DNA (M-DNA), and *M. phlei* cell wall complex (MCC). Compounds which can serve as emulsifiers include natural and synthetic emulsifying agents, as well as anionic, cationic and nonionic compounds. Among the synthetic compounds, anionic emulsifying agents include, for example, the potassium, sodium and ammonium salts of lauric and oleic acid, the calcium, magnesium and aluminum salts of fatty acids, and organic sulfonates such as sodium lauryl sulfate. Synthetic cationic agents include, for example, cetyltrhethylammonium bromide, while synthetic nonionic agents are exemplified by glycerylesters (e.g., glyceryl monostearate), polyoxyethylene glycol esters and ethers, and the sorbitan fatty acid esters (e.g., sorbitan monopalmitate) and their polyoxyethylene derivatives (e.g., polyoxyethylene sorbitan monopalmitate). Natural emulsifying agents include acacia, gelatin, lecithin and cholesterol.

Other suitable adjuvants can be formed with an oil component, such as a single oil, a mixture of oils, a water-in-oil emulsion, or an oil-in-water emulsion. The oil can be a mineral oil, a vegetable oil, or an animal oil. Mineral oils are liquid hydrocarbons obtained from petrolatum via a distillation technique, and are also referred to in the art as liquid paraffin, liquid petrolatum, or white mineral oil. Suitable animal oils include, for example, cod liver oil, halibut oil, menhaden oil, orange roughy oil and shark liver oil, all of which are available commercially. Suitable vegetable oils, include, for example, canola oil, almond oil, cottonseed oil, corn oil, olive oil, peanut oil, safflower oil, sesame oil, soybean oil, and the like. Freund's Complete Adjuvant (PCA) and Freund's Incomplete Adjuvant (FIA) are two common adjuvants that are commonly used in vaccine preparations, and are also suitable for use in the present invention. Both FCA and FIA are water-in-mineral oil emulsions; however, FCA also contains a killed *Mycobacterium* sp.

Immunomodulatory cytokines can also be used in the vaccine compositions to enhance vaccine efficacy, for example, as an adjuvant. Non-limiting examples of such cytokines include interferon alpha (IFN-α) interleukin-2 (IL-2), and granulocyte macrophage-colony stimulating factor (GM-CSF), or combinations thereof.

The vaccine composition can be prepared using techniques well known to those skilled in the art including, but not limited to, mixing, sonication and microfluidation. The adjuvant can comprise from about 10% to about 80% (v/v) of the vaccine composition, more preferably about 20% to about 50% (v/v), and more preferably about 20% to about 30% (v/v), or any integer within these ranges.

The vaccine composition can be administered to any animal, and preferably is a mammal such as a human, mouse, rat, hamster, guinea pig, rabbit, cat, dog, monkey, cow, horse, pig, and the like. Humans are most preferred.

Administration of the vaccine composition can be by infusion or injection (e.g., intravenously, intramuscularly, intracutaneously, subcutaneously, intrathecal, intraduodenally, intraperitoneally, and the like). The vaccine composition can also be administered intranasally, vaginally, rectally, orally, intratonsilar, or transdermally. Additionally, the vaccine composition can be administered by "needle-free" delivery systems.

The effective amount of the vaccine composition may be dependent on any number of variables, including without limitation, the species, breed, size, height, weight, age, overall health of the patient, the type of formulation, or the mode or manner or administration. The appropriate effective amount can be routinely determined by those of skill in the art using routine optimization techniques and the skilled and informed judgment of the practitioner and other factors evident to those skilled in the art. Preferably, a therapeutically effective dose of the vaccine composition described herein will provide the therapeutic preventive benefit without causing substantial toxicity to the subject.

The vaccine composition can be administered to a patient on any schedule appropriate to induce and/or sustain an immune response against *Shigella* or any other protein of interest. For example, patients can be administered a vaccine composition as a primary immunization as described and exemplified herein, followed by administration of a secondary immunization, or booster, to bolster and/or maintain protective immunity.

The vaccine administration schedule, including primary immunization and booster administration, can continue as long as needed for the patient, for example, over the course of several years, to over the lifetime of the patient. The frequency of primary vaccine and booster administration and dose administered can be tailored and/or adjusted to meet the particular needs of individual patients, as determined by the administering physician according to any means suitable in the art.

The vaccine composition may be administered prophylactically (before exposure to *Shigella*, EIEC, or other foreign pathogen) or therapeutically (after exposure to *Shigella*, EIEC, or other foreign pathogen).

6. Methods of Inducing an Immune Response

In another aspect, the vaccine strain or vaccine composition can be used in a method of inducing an immune response. The immune response can be induced in a naïve subject who has not previously been exposed to *Shigella* or EIEC (or some other foreign pathogen). Alternatively, the immune response can be induced in a subject who has been previously exposed to *Shigella* or EIEC (or some other foreign pathogen) and used to enhance an existing immune response.

In one embodiment, the method comprises administering to a subject a vaccine strain or a vaccine composition, wherein the administration of the vaccine strain or the vaccine composition induces an immune response against a protein, or immunogenic portion thereof, encoded by the recombinant vector in the vaccine strain or the vaccine composition.

In certain embodiments, the recombinant vector comprises a nucleic acid encoding a foreign protein, or an immunogenic portion thereof, as discussed previously. In other embodiments, the recombinant vector comprises a nucleic acid encoding a *Shigella* or EIEC protein, or an immunogenic portion thereof, as discussed previously. Alternatively, the recombinant vector may comprise a first nucleic acid encoding a foreign protein, or immunogenic portion thereof, and a second nucleic acid encoding a *Shigella* or EIEC protein, or immunogenic portion thereof.

One embodiment is directed to a method of inducing an immune response against *Shigella* or EIEC in a subject, the method comprising administering to the subject a vaccine strain or a vaccine composition in an amount sufficient to induce an immune response to *Shigella* or EIEC in the subject. In certain aspects, the vaccine strain or the vaccine composition induces significantly less transepithelial migration of polymorphonuclear neutrophils (PMNs), as compared to the 2457T *Shigella flexneri* strain or, in certain embodiments, does not induce transepithelial migration of PMNs. Transepithelial migration of PMNs can be measured using routine methods, such as those described in this application.

Another embodiment is directed to a method of inducing an immune response to a bacterial, viral, fungal, parasitic, or mammalian protein in a subject, the method comprising administering to the subject a vaccine strain or a vaccine composition in an amount sufficient to induce an immune response to the bacterial, viral, fungal, parasitic, or mammalian protein in the subject.

In these methods of inducing an immune response, the immune response can be measured using routine methods in the art, such as those disclosed in this application. These routine methods include, but are not limited to, measuring an antibody response, such as an antibody response directed against the protein encoded by the recombinant vector, and measuring cellular proliferation, including, for example, by measuring tritiated thymidine incorporation or cytokine (e.g., IFN-γ) production.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1

Construction of SMIP

A core plasmid called SMIP for *Shigella* minimum invasion plasmid was constructed comprising the following features:
- an IncF-type low copy number replicon to mimic the low copy number of the *Shigella* virulence plasmid;
- genes for the *Shigella* invasion effectors, ipa-ipg, and genes for the *Shigella* T3SS, i.e. mxi-spa;
- genes for the positive activators virB and virF from the *Shigella* virulence plasmid.

an antibiotic resistance gene for selection of transfer of the SMIP into different strain backgrounds; and an inducible high-copy control replicon, oriV, for improving plasmid DNA yields while maintaining plasmid stability.

With the exception of virF, all of the *Shigella* genes on the SMIP are contained within a contiguous stretch of about 30 kb on the *Shigella* virulence plasmid called the cell entry region. The virF gene, which encodes a transcriptional activator of the *Shigella* invasion plasmid genes, is separated from the cell entry region by about 62 kb. The virF gene was introduced in a separate step in the SMIP construction.

The plasmid backbone is the copy control vector pCClFOS (Epicentre Biotechnologies, Madison, Wis.). It replicates as a single copy (oriF) but is inducible to 50 copies in a special *E. coli* host cell which carries of trfA under pBAD induction to drive oriV on pCClFOS. This plasmid can accept insert sizes of about 40 kb and is thus capable of accepting the cluster of genes described above.

First, the virF gene was added to the pCClFOS backbone. More specifically, virF was amplified by PCR from the virulence plasmid in *S. flexneri* 2a strain 2457T such that BlpI and Eco47III ends were added to the PCR product. Next, virF was cloned into pCClFOS at the unique BlpI and Eco47III sites (base 4468 and 4555, respectively) on pCClFOS.

After cloning the virF gene into pCClFOS, the virB-ipa-mxi-spa region of virulence plasmid of *S. flexneri* 2a strain 2457T was cloned into pCClFOS-virF. More specifically, recombination mediated by lambda red was used to sequentially introduce SfiI sites flanking the virB-ipa-mxi-spa region of the invasion plasmid in *S. flexneri* 2a strain 2457T. An SfiI site and chloramphenicol resistance marker (cat) were introduced upstream of ipaJ. The chloramphenicol resistance marker was removed by FLP mediated recombination between the FRT sites that flanked the cat cassette. An SfiI site and kanamycin resistance marker (kan) were introduced downstream of orf131b. The kanamycin resistance marker was left in for later selection when cloning into pCClFOS. The recombinant plasmid was isolated from the host strain, digested with SfiI and the approximately 35 kb SfiI fragment containing the ipaJ-ipa-mxi-orf131b region was recovered. The approximately 35 kb SfiI fragment containing the ipaJ-ipa-mxi-orf131b region was ligated into the SfiI site in pCClFOS-virF and the recombinant molecule was packaged in vitro into lambda particles. The lambda particles were used to transduce *E. coli* EPI300 with selection for kanamycin and chloramphenicol resistance to create an *E. coli* host strain EPI300 carrying the SMIP.

Example 2

Transfer of SMIP to Plasmid-Cured Strain of *Shigella*

SMIP DNA was isolated from the *E. coli* host strain EPI300. The isolated SMIP was transformed by electroporation into a plasmid-cured strain of *S. flexneri* 2a (BS103) with selection for kanamycin and chloramphenicol resistance. The invasion phenotype of BS103/SMIP was measured in tissue culture monolayers by standard methods to quantify invasion and intracellular growth of bacteria post-invasion.

Example 3

Antigen-Specific Antibody Responses in SMIP Immunized Guinea Pigs

Three groups of male Hartley guinea pigs were immunized in the eyes at $D_0$ (primary immunization) and $D_{14}$ (secondary immunization) with either 0.9% saline (n=8), about $5 \times 10^8$ SMIP (n=6), or about $5 \times 10^8$ SMIP/virG(icsA) (n=6). The immunizing strain was a virulence plasmid-cured strain of *S. flexneri* 2a that had been transformed with the Smip, i.e., strain BS875. Mucosal washes from the eyes were obtained at $D_0$, $D_{14}$ (14 days after primary immunization), and $D_{28}$ (14 days after secondary immunization). Serum samples were obtained at $D_0$, $D_{14}$ (14 days after primary immunization), $D_{28}$ (14 days after secondary immunization), and $D_{55}$ (14 days after challenge with about $5 \times 10^8$ of *Shigella flexneri* 2457T).

Figure 1A:
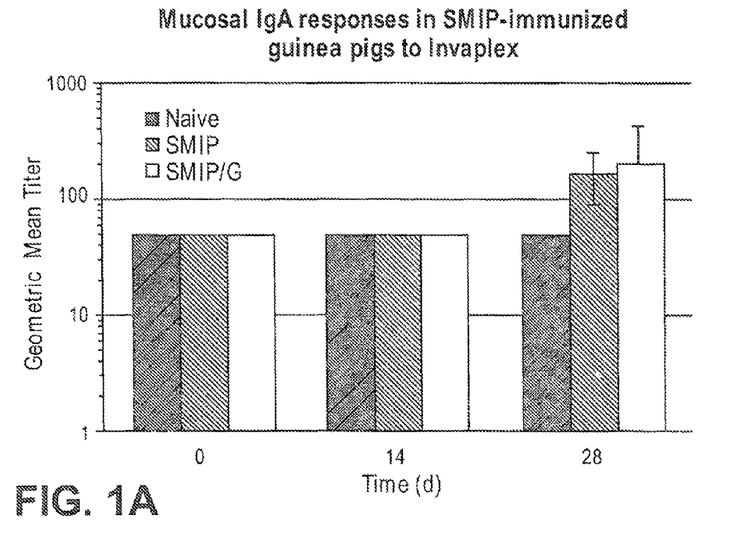
Figure 1B:
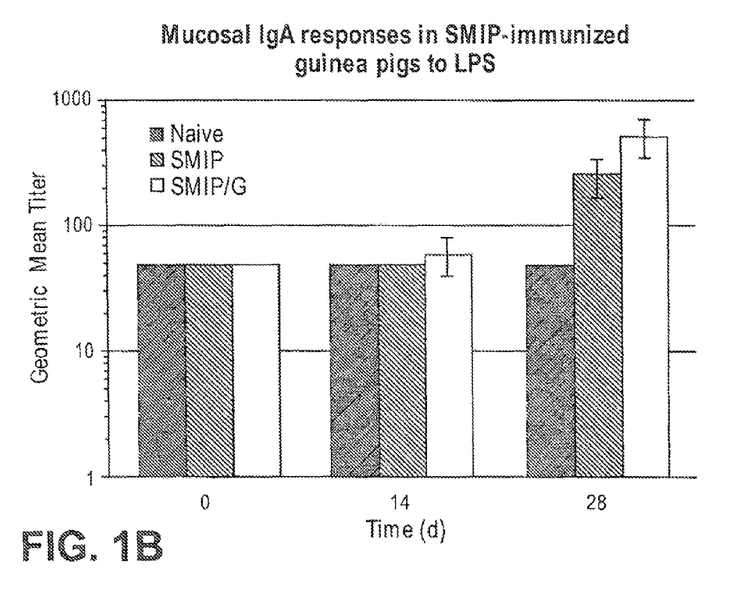
Figure 2A:
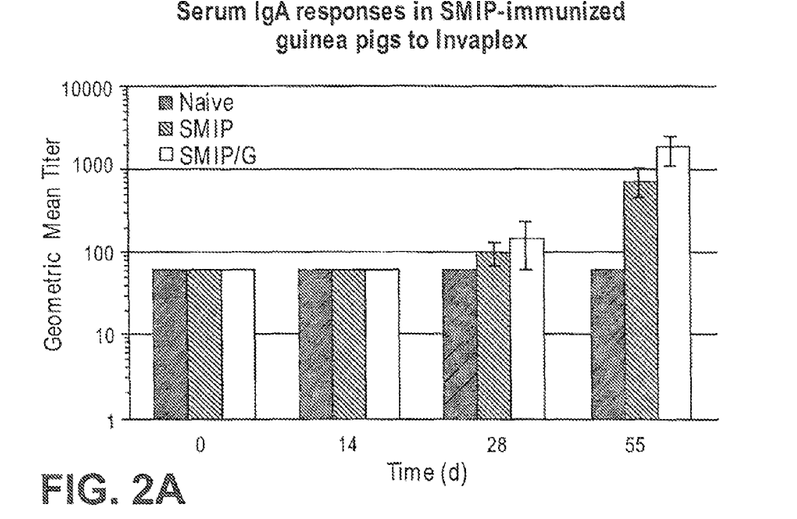
Figure 2B:
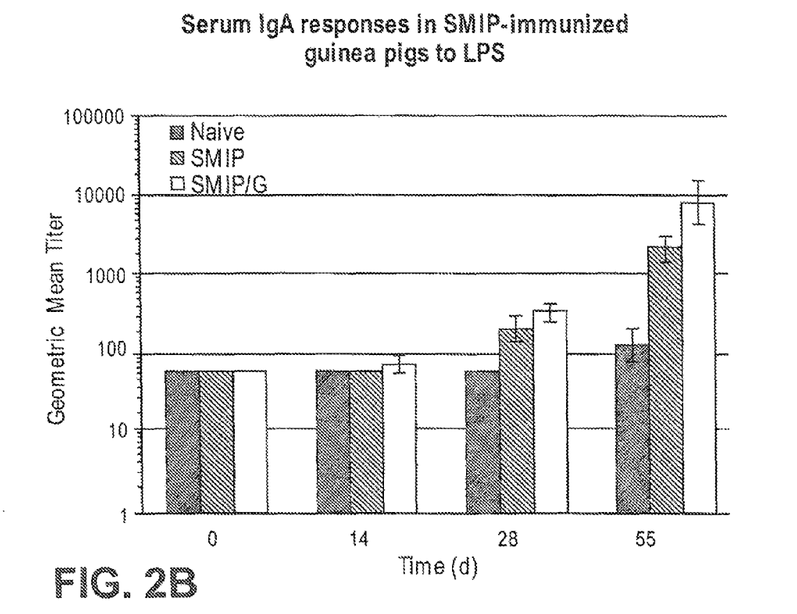
Figure 3A:
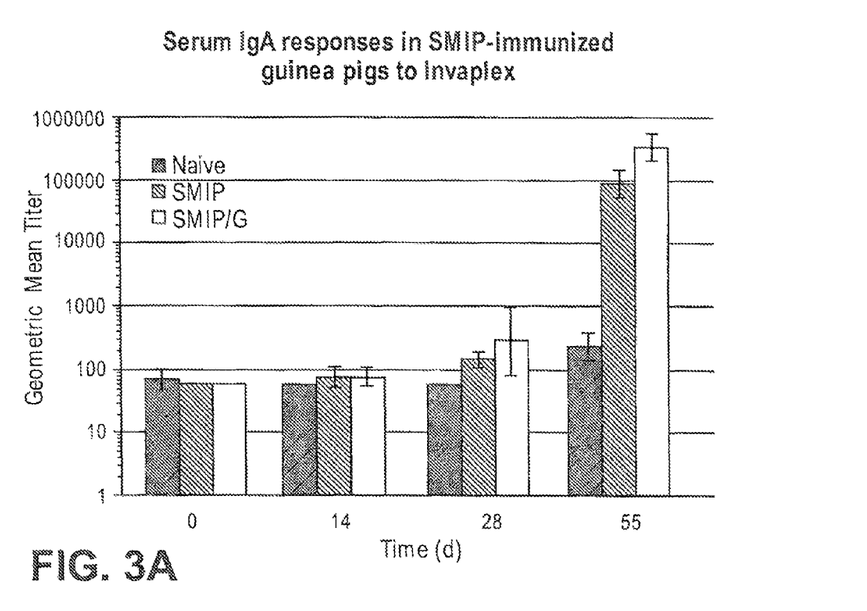
Figure 3B:
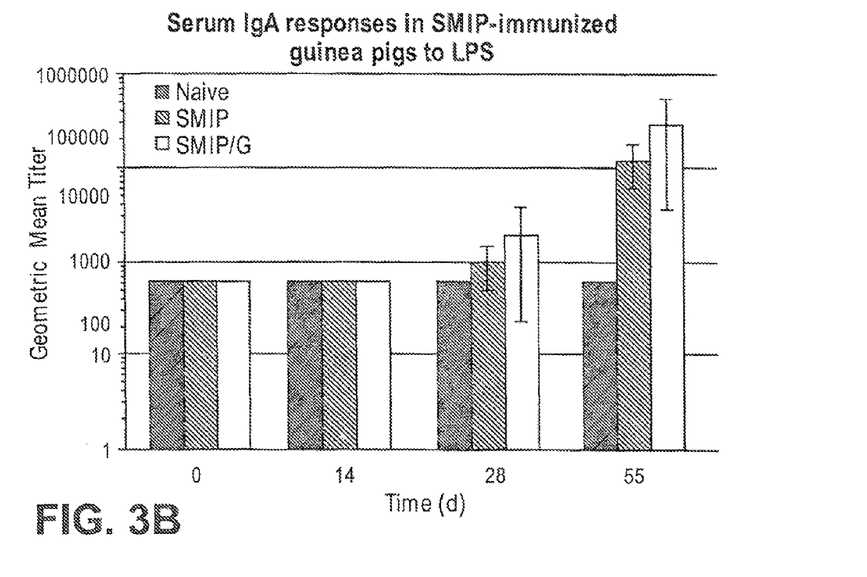

Geometric mean titers (GMT) of mucosal and serum IgA responses and serum IgG specific for lipopolysaccharide (LPS) or Invaplex (crude water-extracted *Shigella*) were determined by indirect ELISA. FIGS. 1-3. Guinea pigs immunized with SMIP constructs, with or without virG (icsA), showed much higher IgA and IgG responses to LPS and Invaplex as compared to a naïve guinea pig, demonstrating the utility of the SMIP construct for vaccine development FIGS. 1-3.

Example 4

Polymorphonuclear Neutrophil (PMN) Migration

PMNs are phagocytes that endocytose and kill extracellular pathogens, like bacteria. PMN transepithelial migration is used as a marker for an inflammatory response. The PMN migration assay was carried out as described by McCormick et al. 1998. Infect. Immun. 66:4237-4243. Briefly, *Shigella* cells were added to the basolateral side of 0.33-cm² tray at an MOI of about 100 for 90 min. A chemotactic peptide (fLMP) was used as a positive control. Cells were washed and then incubated in fresh medium containing gentamicin (50 µg/ml) for 90 min. PMN were added to the basolateral compartment, and transmigration to the apical compartment was quantified by assaying for the PMN azurophilic granule marker myeloperoxidase. All values were expressed as cell equivalents (CE)×10,000.

Figure 4:
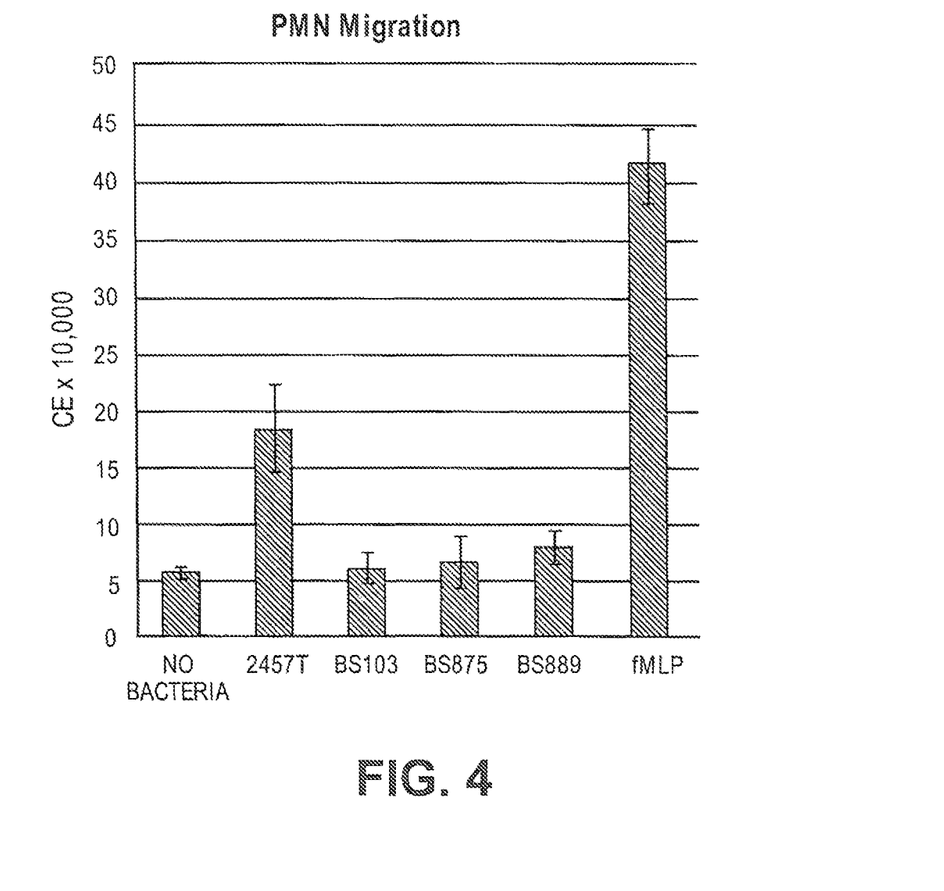
FIG. 4 shows the transepithelial migration of polymorphonuclear neutrophils (PMNs) in response to 2457T (wild type *Shigella flexneri*), BS103 (virulence plasmid-cured 2457T), BS875 (BS103 carrying SMIP), BS889 (BS103 carrying SMIP+virG(icsA)), and fMLP (a chemotactic peptide). All values were expressed as cell equivalents (CE)× 10,000.

FIG. 4 shows the transepithelial migration of PMNs in response to 2457T (wild type *Shigella flexneri*), BS103 (virulence plasmid-cured 2457T), BS875 (BS103 carrying SMIP), BS889 (BS103 carrying SMIP+virG(icsA)), and fMLP (a chemotactic peptide). All values were expressed as cell equivalents (CE)×10,000. As seen in FIG. 4, unlike the 2457T *Shigella flexneri* strain, the SMIP strains do not induce PMN migration. These results show that SMIP is less reactogenic than a wild type strain of *Shigella* and suggest that SMIP, when used as a vaccine, will be less reactogenic than a conventionally attenuated strain of *Shigella*.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed:

1. A recombinant vector comprising a cell entry region from a *Shigella* invasion plasmid and a virF gene from a *Shigella* invasion plasmid,
   wherein the recombinant vector has no more than about 30-50 kilobase pairs of a *Shigella* invasion plasmid, and wherein the cell entry region comprises an ipa gene locus, an ipg gene locus, a virB gene, and a mxi-spa gene locus.

2. The recombinant vector of claim 1, further comprising a selection gene.

3. The recombinant vector of claim 1, further comprising a virG(icsA) gene from a *Shigella* bacterium.

4. The recombinant vector of claim 1, wherein the vector does not contain an osp gene from a *Shigella* invasion plasmid.

5. The recombinant vector of claim 1, wherein the vector has no more than about 40-100 kilobase pairs.

6. The recombinant vector of claim 1, further comprising a nucleic acid encoding a *Shigella* protein, or a portion thereof, wherein the *Shigella* protein is not encoded by an ipa gene locus, an ipg gene locus, a virB gene, a mxi-spa gene locus, a virF gene, or a virG(icsA) gene.

7. The recombinant vector of claim 1, wherein the *Shigella* cell-entry region is from a *Shigella flexneri* bacterium.

8. The recombinant vector of claim 1, further comprising a low copy origin of replication and a high copy origin of replication.

9. The recombinant vector of claim 2, wherein the selection gene is an antibiotic resistance gene.

10. The recombinant vector of claim 1, further comprising a nucleic acid encoding a bacterial, viral, fungal, parasitic, or mammalian protein or a portion thereof.

11. A *Shigella* or *E. coli* bacterium comprising the recombinant vector of claim 1, wherein the *Shigella* or *E. coli* bacterium is a plasmid-cured bacterium.

12. A *Shigella* or *E. coli* bacterium comprising the recombinant vector of claim 10, wherein the *Shigella* or *E. coli* bacterium is a plasmid-cured bacterium.

13. A composition comprising the *Shigella* or *E. coli* bacterium of claim 11 and a pharmaceutically acceptable excipient.

14. The composition of claim 13, further comprising an adjuvant.

15. A composition comprising the *Shigella* or *E. coli* bacterium of claim 12 and a pharmaceutically acceptable excipient.

16. The composition of claim 15, further comprising an adjuvant.

17. A method of inducing an immune response to *Shigella* in a subject, the method comprising administering the composition of claim 13 to the subject in an amount sufficient to induce an immune response to *Shigella* in the subject.

* * * * *

UNITED STATES PATENT AND TRADEMARK OFFICE
CERTIFICATE OF CORRECTION

| | | |
|---|---|---|
| PATENT NO. | : 9,434,772 B2 | Page 1 of 1 |
| APPLICATION NO. | : 14/346408 | |
| DATED | : September 6, 2016 | |
| INVENTOR(S) | : Anthony T. Maurelli | |

It is certified that error appears in the above-identified patent and that said Letters Patent is hereby corrected as shown below:

In The Specification

In Column 1, lines 16-19, please delete

"This invention was made in part with Government support under grant R01 AI24656-18 awarded by the National institute of Allergy and Infectious Diseases. The U.S. Government has certain rights in this invention."

and insert

--This invention was made with government support under grant number AI024656 awarded by the National Institutes of Health. The government has certain rights in the invention.--

Signed and Sealed this
Twenty-ninth Day of November, 2016

Michelle K. Lee
*Director of the United States Patent and Trademark Office*